(12) United States Patent
Cano

(10) Patent No.: US 10,905,386 B2
(45) Date of Patent: Feb. 2, 2021

(54) ORIENTING X-RAY PROJECTION FOR DENTAL IMAGERY

(71) Applicant: Suzanne Cano, Apex, NC (US)

(72) Inventor: Suzanne Cano, Apex, NC (US)

( * ) Notice: Subject to any disclaimer, the term of this patent is extended or adjusted under 35 U.S.C. 154(b) by 0 days.

(21) Appl. No.: 15/916,934

(22) Filed: Mar. 9, 2018

(65) Prior Publication Data

US 2019/0274643 A1 Sep. 12, 2019

(51) Int. Cl.
*A61B 6/14* (2006.01)
*A61B 6/00* (2006.01)

(52) U.S. Cl.
CPC .............. *A61B 6/14* (2013.01); *A61B 6/4064* (2013.01); *A61B 6/466* (2013.01); *A61B 6/405* (2013.01); *A61B 6/548* (2013.01); *A61B 6/587* (2013.01)

(58) Field of Classification Search
CPC ........... A61B 6/00; A61B 6/032; A61B 6/035; A61B 6/14; A61B 6/145; A61B 6/42; A61B 6/4208; A61B 6/425; A61B 6/4275; A61B 6/4283; A61B 6/589; A61B 6/588; A61B 6/587; A61B 6/501; A61B 6/4423; A61B 6/4417; A61B 6/44; G03B 42/042; G03B 42/04; G01N 2800/18; G01N 23/083; G01N 23/06; G01N 23/02; G01N 23/00

See application file for complete search history.

(56) References Cited

U.S. PATENT DOCUMENTS

| | | | | |
|---|---|---|---|---|
| 2004/0218792 | A1* | 11/2004 | Spoonhower | A61B 5/0084 382/128 |
| 2008/0144778 | A1* | 6/2008 | Sonani | A61B 6/08 378/206 |
| 2010/0106056 | A1* | 4/2010 | Norris | A61B 8/0841 600/567 |

* cited by examiner

*Primary Examiner* — David P Porta
*Assistant Examiner* — Mamadou Faye
(74) *Attorney, Agent, or Firm* — James A. Italia; Italia IP

(57) ABSTRACT

Apparatus for aiming e.g. an X-ray camera, for capturing image(s) of a physiology of a patient, and related method, are shown and described. A plurality of light projectors are mounted to the X-ray camera. When projected light beams impinge upon pre-identified reference points on the physiology of the patient, a visual indicator operates to indicate that the X-ray image may be taken. The pre-identified reference points may exist within a microprocessor associated with the X-ray camera, and may be based on an image of the physiology. The microprocessor maps the reference points to small indication areas illuminated by the light projectors. When a predetermined threshold of registration of the indication areas with the reference points exists, the visual indicator operates, whereupon the human operator may operate the X-ray camera.

14 Claims, 3 Drawing Sheets

ORIENTING X-RAY PROJECTION FOR DENTAL IMAGERY

FIELD OF THE INVENTION

The present invention relates to medical imagery such as X-rays, and more particularly, to a system for aiming energy such as X-rays for medical imagery.

BACKGROUND OF THE INVENTION

Dental X-rays, such as of the mouth, are performed by having a dental practitioner manually aim the ray projector towards a patient. However, this can lead to inaccuracies that render the resulting image impaired or even useless. Dentsply Rinn Corporation has provided holders for assuring that X-ray film will be held at an appropriate orientation for image capture. However, such products may induce discomfort in patients.

There exists a need in the art for an improved way of orienting X-rays to patient anatomy that overcomes discomfort issues.

SUMMARY OF THE INVENTION

The present invention eliminates Dentsply Rinn type holders in favor of calculating proper orientation of an X-ray emitter. A plurality of points or locations on the physiology of a patient are signaled by miniature laser projectors. Independently of illuminated patches of light on the physiology of the patient resulting from the miniature lasers, these locations are placed into alignment with reference points contained within a microprocessor as the X-ray emitter is maneuvered. The system recognizes appropriate alignment and signals to the human operator that the X-ray device is in the proper position and that the image may be taken. The illuminated patches enable rough adjustments, with fine final adjustments made by calculation using a microprocessor. Internal data processing identifies acceptable accuracy of the direction of the X-ray emitter, upon attainment of which the signal is generated.

The present invention provides improved elements and arrangements thereof by apparatus for the purposes described which is inexpensive, dependable, and fully effective in accomplishing its intended purposes.

These and other objects of the present invention will become readily apparent upon further review of the following specification and drawings.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION

Figure 1:
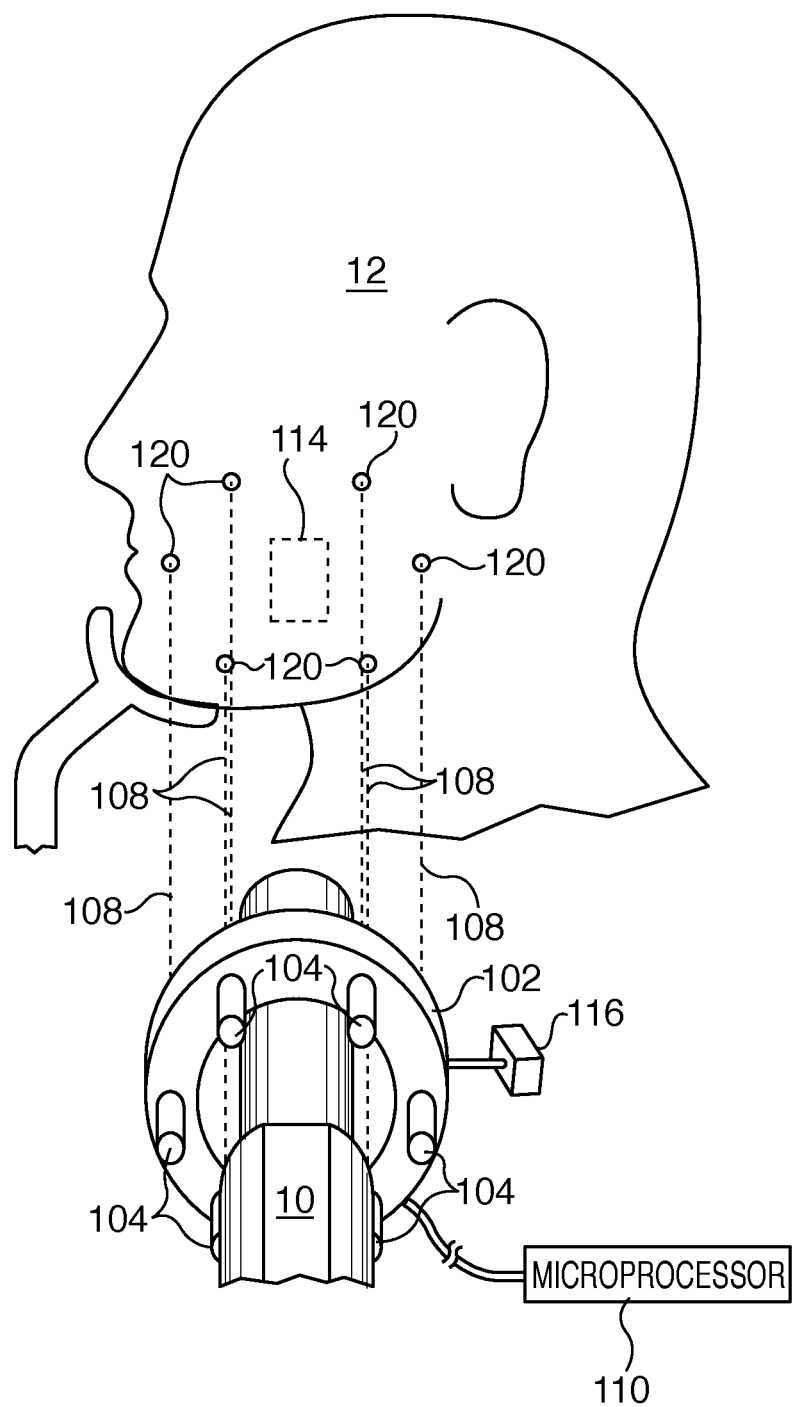
FIG. 1 is a diagrammatic environmental representation of an X-ray camera being focused on a human subject.
Figure 2:
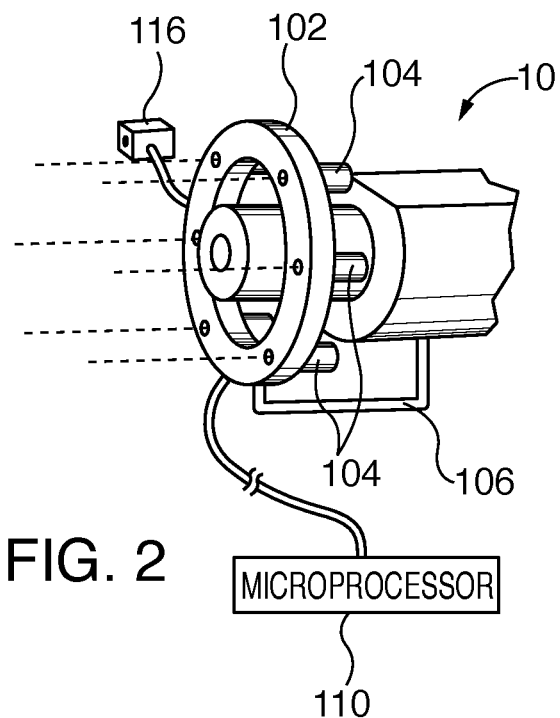
FIG. 2 shows the X-ray camera from a perspective different from that of FIG. 1.

Referring to FIGS. 1 and 2, according to at least one aspect of the invention, there is shown apparatus 100 for aiming a radiant energy projector 10 for capturing one or more desired images of a physiology of a patient 12 using radiant energy projector 10. Apparatus 100 may comprise a chassis 102 including a plurality of lighting projectors 104, and a mounting 106 enabling securing of chassis 102 on radiant energy projector 10 such that lighting projectors 104 are aimed parallel to an axis 108 of radiant energy projected from radiant energy projector 10.

Apparatus 100 may also comprise a microprocessor 110 having computer instructions loaded thereinto for comparing positional data of radiant energy projector 10 to predetermined positional data of patient 12, and to determine alignment of radiant energy projector 10 with patient 12, and an automated indicator actuatable by microprocessor 110 to indicate when the positional data of radiant energy projector 10 is aligned with patient 12. Optionally, apparatus 100 may comprise a holder 112 operable to secure the physiology of patient 12 in a constant location relative to radiant energy projector 10. Holder 112 is optional because there are ways to determine alignment of radiant energy projector 10 with patient 12 other than those utilizing holder 12, as will be further explained hereinafter.

Radiant energy projector 10 may be an X-ray emitter or a CT signal emitter for example. A desired image is that image which captures a specific targeted portion of the physiology for dental or medical analysis, such as an X-ray image of a tooth site. Chassis 102 may be a ring as depicted herein, or any other rigid structure capable of holding lighting projectors 104 in a position such that lighting projectors 104 will emit light in an array such as that indicated by axes 108 of projected light.

Mounting 106 is depicted as an arm attached to chassis 102 and to radiant energy projector 10, but may take other forms. Illustratively, mounting 106 may comprise clips, clamps, threaded fasteners, friction fit and/or other devices capable of holding chassis 102 to radiant energy projector 10 in a constant orientation or position.

The automated indicator may be a discrete element unto itself (this option is not shown), or alternatively, may be realized by manipulating lighting characteristics of light produced by lighting projectors 104, as will be described hereinafter.

Holder 112 is depicted as a chin support in FIG. 1, but may take other forms. Any device which supports, holds, or restrains patient 12 in a suitably fixed location for capturing the desired image will suffice. It will be recognized that the desired image will be produced by an energy responsive image forming medium 114, such as X-ray film placed in the mouth of patient 12 in conventional manner.

Patient 12, although depicted as human, may be an animal.

The computer instructions may be based on a predetermined geometric relationship between radiant energy projector 10 and a patient 12 held in holder 112. That is, distance and azimuthal orientation of radiant energy projector 10 and patient 12 in holder 112 may be determined beforehand and loaded into memory (not separately shown) of microprocessor 110. For example, such instructions may be based upon entered data of the patient 12 based at least in part on sex, age, simple measurements, and/or any other form of data of the patient 12.

Alternatively, the computer instructions may be based on an image of the physiology of patient 12. In this case, an image of the physiology of patient 10 is captured, either by a camera integrated with apparatus 100 or separate therefrom. The resulting image, as a digital photograph or 3D scan, or possibly a CT scan, would yield data in the form of a data plot or topography plot. This data would then be processed to generate a signal annunciating acceptable positioning of radiant energy projector 10, as will be further explained hereinafter. Hence the computer instructions may include data corresponding to at least simple data of a patient (age, sex, simple measurements, etc.) or more precise data plots, such as, topography plots which may be derived from the image or scan of the physiology of patient 12.

It will be recognized that due to the diagrammatic nature of FIGS. 1 and 2, some components are not shown. Illustratively, although microprocessor 110 is shown connected to chassis 102 by a cable 118, other connecting circuitry is not illustrated. Accordingly, apparatus 100 will be understood to include necessary power source, power and control circuitry, and operator controls (none of these elements are shown) to arrive at a system functional as described.

It is possible that apparatus 100 may further comprise an image capture device 116 in communication with microprocessor 110, whereby apparatus 100 can obtain the image of the physiology of patient 12 independently of a separate camera or other image capture device such as a cellular telephone (none of these options is shown).

Figure 3:
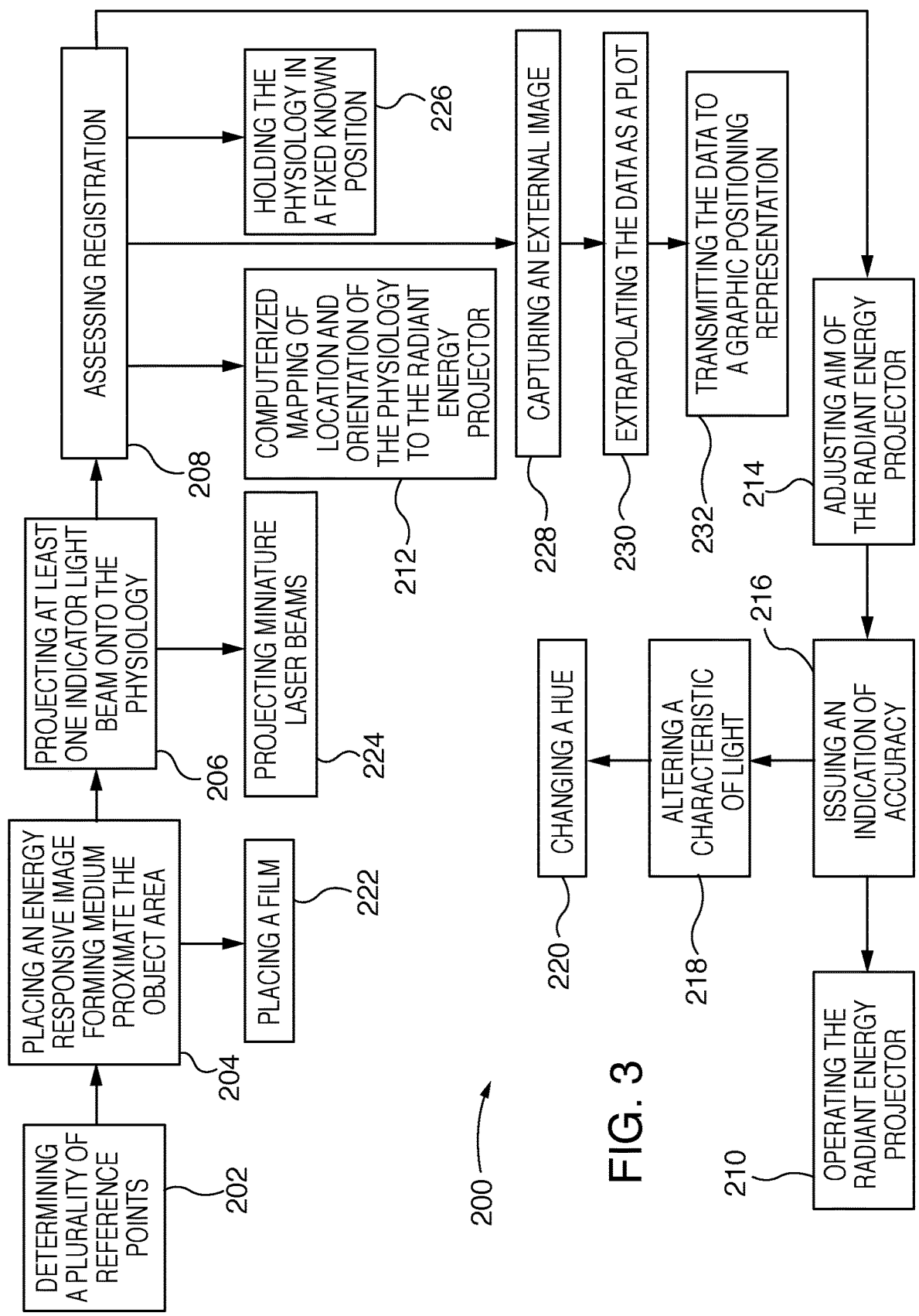
FIG. 3 is a flow chart showing steps of a method of aiming a radiant energy projector, wherein the steps are abbreviated.

Reference is now made to FIG. 3, showing steps of a method 200 in abbreviated form. Use of apparatus 100 will now be explained in terms of method 200, method 200 for aiming radiant energy projector 10 for capturing one or more desired image(s) of a physiology of patient 12, where the radiant energy is to be projected toward an object area of the physiology, the object area being an object of interest to be captured in the desired image(s). Method 200 may comprise determining a plurality of reference points on the external surface of the physiology in the external image, wherein each one of the reference points is laterally displaced from the object area relative to a direction of radiant energy to be projected (see block 202 in FIG. 3). The method may further comprise placing a film (energy responsive image forming medium 114) against the object area of the physiology, wherein the film will generate an image when the radiant energy impinges thereon (block 204). Method 200 may also comprise, with lighting projectors 104 projecting the at least one indicator light beam fixed to radiant energy projector 10, projecting at least one indicator light beam onto the physiology to generate an equal number of illuminated areas 120 on the physiology (block 206). The method may further comprise assessing registration of illuminated areas 120 with the reference points, and operating radiant energy projector 10 to project radiant energy to generate the desired image(s) in energy responsive image forming medium 114 when assessed registration of illuminated areas 120 with the reference points meets a predetermined threshold of accuracy (block 208).

The object area may be for example a tooth site possibly concealed behind the cheeks and lips of a patient upon which an image forming medium 114 (e.g., an X-ray film) has been placed behind. Because the object area is concealed, the novel method enables successful aiming of radiant energy projector 10 (e.g., an X-ray emitter).

The external image mentioned above, not to be confused with the desired image, is a convenience for establishing reference points, and is utilized to determine when radiant energy projector 10 is correctly aimed. This image may be utilized wherein assessing registration of illuminated areas 120 with the reference points comprises computerized mapping of location and orientation of the physiology to location and orientation of radiant energy projector 10 (block 212). If insufficient registration is encountered, the method may further comprise adjusting aim of radiant energy projector 10 to align the reference points of the physiology with illuminated areas 120 generated by the indicator light beam to meet the predetermined threshold of accuracy, and issuing an indication of accuracy when illuminated areas 120 generated by the indicator light beam are aligned with the reference points (block 214). Alignment may be performed by microprocessor 110. The indicator light beams are shown as axis 108.

Note that the external image may be modified by user inputs, such as by inputting patient age, gender, height, weight, and other data. This reduces inaccuracies that might otherwise arise from using a single standard template to represent all physiological types, and reduces the need to better aim radiant energy projector 10.

Issuing the indication of accuracy (block 216) may comprise altering a characteristic of light of illuminated areas 120 (block 218). For example, indicator light beams may be caused to flash, or if emitted as flashing, may be changed to constant projection. In an alternative, altering a characteristic of light of illuminated areas 120 (block 218) may comprise changing a hue of light establishing illuminated areas 120 (block 220).

It would also be possible to have a dedicated audible or visible indicator on chassis 102 or in some other location, or integrated with radiant energy projector 10 (these options are not shown). It would further be possible to forego indicating accuracy, and to actuate radiant energy projector 10 directly, with or without an indicator.

Projecting the indicator light beam may comprise projecting miniature laser beams (block 224). To this end, lighting projectors 104 may comprise miniature laser projectors such as those utilized in rifle sighting and demonstration and lecture pointers.

Assessing registration of illuminated areas 120 with the reference points may comprise holding the physiology of patient 12 in a fixed, known position relative to radiant energy projector 10, and comparing position of the physiology of patient 12 with the position of radiant energy projector 10 (block 226). Alternatively, assessing registration of illuminated areas 120 with the reference points may comprise capturing an external image of the physiology (block 228), extrapolating the data as a form plot or as a topography plot (block 230), and transmitting the data corresponding to the form or topography plot to a graphic positioning representation (block 232). Alternatively stated, results of the plot may be displayed on a screen or an equivalent.

The method may further comprise capturing an external image of an external surface of the physiology, wherein the object area is concealed from view within the physiology. The external image may be utilized to establish the reference points.

To that end, the film is seen in FIG. 1 as energy responsive image forming medium 114. Alternatively stated, placing the energy responsive image forming medium may comprise placing a film proximate the object area (block 222).

Figure 4:
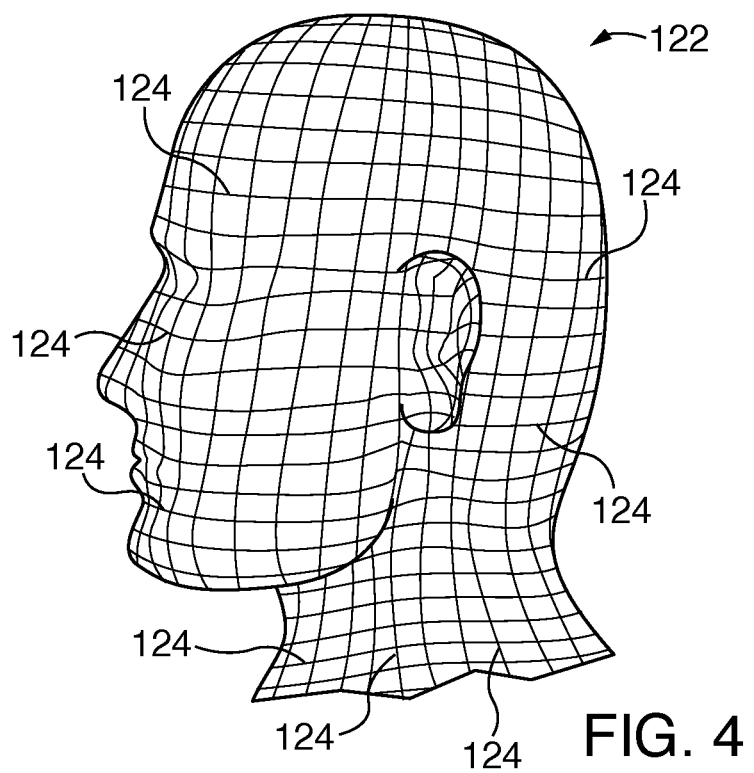
FIG. 4 is a diagrammatic view of a topographic rendering of the patient shown in FIG. 1.

FIG. 4 illustrates a topographic rendering 122 of patient 12 that may be generated though the methods described above. In topographic rendering 122 of FIG. 4, the reference points may be established by intersections of grid members 124.

While the present invention has been described in connection with what is considered the most practical and preferred embodiment, it is to be understood that the present invention is not to be limited to the disclosed arrangements, but is intended to cover various arrangements which are included within the spirit and scope of the broadest possible interpretation of the appended claims so as to encompass all modifications and equivalent arrangements which are possible.

I claim:

1. A method for aiming a radiant energy projector for capturing one or more desired image(s) of a physiology of a patient, where the radiant energy is to be projected toward an object area of the physiology, the object area being an object of interest to be captured in the desired image(s), the method comprising:

determining a plurality of reference points on the external surface of the physiology of the patient using computerized mapping, wherein each one of the reference points is laterally displaced from the object area relative to a direction of radiant energy to be projected;

placing an energy responsive image forming medium proximate the object area of the physiology;

projecting at least one indicator light beam fixed to the radiant energy projector, wherein the step includes projecting at least one indicator light beam onto the physiology of the patient to provide a general idea of the direction of the radiant energy projector toward the physiology of the patient;

utilizing the computer generated plurality of reference points on the surface of the physiology of the patent to assess registration of the radiant energy projector, wherein registration of the radiant energy projector completed when the radiant energy projector is in proper orientation relative to the computer mapped reference points on the physiology of the patient; and operating the radiant energy projector to project radiant energy to generate the desired image(s) in the energy responsive image forming medium when the assessed registration between the radiant energy projector and the reference points mapped on the physiology of the patient meets a predetermined threshold of accuracy.

2. The method of claim 1, further comprising:

adjusting aim of the radiant energy projector to align the reference points of the physiology with the illuminated areas generated by the indicator light beam to assist in meeting the predetermined threshold of accuracy; and issuing an indication of accuracy when the illuminated areas generated by the indicator light beam are aligned with the reference points.

3. The method of claim 2, wherein issuing the indication of accuracy comprises altering a characteristic of light of the illuminated areas.

4. The method of claim 3, wherein altering a characteristic of light of the illuminated areas comprises changing a hue of light establishing the illuminated areas.

5. The method of claim 1, further comprising placing a film against the object area of the physiology, wherein the film will generate an image when the radiant energy impinges thereon.

6. The method of claim 1, wherein projecting an indicator light beam comprises projecting miniature laser beams.

7. The method of claim 1, wherein assessing registration of the radiant projector relative to the reference points on the physiology of the patient comprises:

capturing an external image of the physiology;

extrapolating the data as a form plot or as a topography plot; and transmitting the data corresponding to the form or topography plot to a graphic positioning representation.

8. The method of claim 1, further comprising capturing an external image of an external surface of the physiology, wherein the object area is concealed from view within the physiology.

9. Apparatus for aiming a radiant energy projector for capturing one or more desired image(s) of a physiology of a patient using a radiant energy projector, the apparatus comprising a chassis including a plurality of lighting projectors;

a mounting enabling securing of the chassis on the radiant energy projector such that the lighting projectors are aimed parallel to an axis of radiant energy projected from the radiant energy projector;

a microprocessor having computer instructions loaded thereinto for comparing positional data of the radiant energy projector to predetermined positional data of the patient, wherein the positional data of the patient is generated by utilizing computer mapping information that generates a plurality of reference points on the surface of the physiology of the patent, and to use both the positional data of the radiant energy projector and the predetermined positional data of the patient to determine proper alignment of the radiant energy projector with the patient; and an automated indicator actuatable by the microprocessor to indicate when the positional data of the radiant energy projector is aligned with the positional data of the patient.

10. The apparatus of claim 9, further comprising a holder able to secure the physiology of the patient in a constant location relative to the radiant energy projector.

11. The apparatus of claim 9, wherein the computer instructions are based on a predetermined geometric relationship between the radiant energy projector and the holder.

12. The apparatus of claim 9, wherein the computer instructions are based on an image of the physiology of the patient.

13. The apparatus of claim 12, wherein the computer instructions include data corresponding to at least one of a form plot and a topography plot based on the image of the physiology of the patient.

14. The apparatus of claim 12, further comprising an image capture device in communication with the microprocessor, whereby the apparatus can obtain the image of the physiology of the patient independently.

* * * * *